(12) United States Patent
Morikazu et al.

(10) Patent No.: US 9,530,929 B2
(45) Date of Patent: *Dec. 27, 2016

(54) LIFT-OFF METHOD (71) Applicant: DISCO CORPORATION, Tokyo (JP)

(72) Inventors: Hiroshi Morikazu, Tokyo (JP); Tasuku Koyanagi, Tokyo (JP); Shin Tabata, Tokyo (JP)

(73) Assignee: DISCO CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/606,488

(22) Filed: Jan. 27, 2015

(65) Prior Publication Data

US 2015/0221818 A1 Aug. 6, 2015

(30) Foreign Application Priority Data

Jan. 31, 2014 (JP) ................................. 2014-016939

(51) Int. Cl.
*H01L 33/00* (2010.01)
*H01S 5/02* (2006.01)
(Continued)

(52) U.S. Cl.
CPC ....... *H01L 33/0079* (2013.01); *H01L 33/0066* (2013.01); *H01L 33/0075* (2013.01);
(Continued)

(58) Field of Classification Search
None
See application file for complete search history.

(56) References Cited

U.S. PATENT DOCUMENTS

2003/0087476 A1* 5/2003 Oohata ................ G09F 9/33
438/108
2007/0275544 A1 11/2007 Maki et al.
(Continued)

FOREIGN PATENT DOCUMENTS

JP 10-305420 11/1998
JP 2004-072052 3/2004
(Continued)

OTHER PUBLICATIONS

U.S. Appl. No. 14/612,732, filed Feb. 3, 2015.
U.S. Appl. No. 14/716,149, filed May 19, 2015.
U.S. Appl. No. 14/798,011, filed Jul. 13, 2015.

*Primary Examiner* — Fernando L Toledo
*Assistant Examiner* — Valerie N Newton
(74) *Attorney, Agent, or Firm* — Greer Burns & Crain, LTD.

(57) ABSTRACT

A lift-off method transfers an optical device layer in an optical device wafer to a transfer substrate. The optical device layer is formed on the front side of an epitaxy substrate through a buffer layer. A composite substrate is formed by bonding the transfer substrate through a bonding agent to the front side of the optical device layer, thereby forming a composite substrate. The buffer layer is broken up by applying a laser beam having a wavelength transmissive to the epitaxy substrate and absorptive to the buffer layer from the back side of the epitaxy substrate to the buffer layer after performing the composite substrate forming step, thereby breaking the buffer layer. An optical device layer is transferred by peeling off the epitaxy substrate from the optical device layer after performing the buffer layer breaking step, thereby transferring the optical device layer to the transfer substrate.

11 Claims, 8 Drawing Sheets

(51) Int. Cl.
  *H01S 5/30* (2006.01)
  *G01N 21/88* (2006.01)

(52) U.S. Cl.
  CPC .......... *H01S 5/0216* (2013.01); *H01S 5/0217* (2013.01); *H01S 5/3013* (2013.01); *G01N 21/88* (2013.01); *H01L 33/007* (2013.01)

(56) References Cited

U.S. PATENT DOCUMENTS

| | | |
|---|---|---|
| 2009/0053845 A1 | 2/2009 | Wong et al. |
| 2009/0253273 A1* | 10/2009 | Sano ................. H01L 21/02683 438/795 |
| 2012/0095584 A1 | 4/2012 | Ando et al. |
| 2012/0168911 A1 | 7/2012 | Chen et al. |
| 2013/0017640 A1 | 1/2013 | Morikazu et al. |
| 2013/0065010 A1 | 3/2013 | Hayashi et al. |

FOREIGN PATENT DOCUMENTS

| | | |
|---|---|---|
| JP | 200472052 | 3/2004 |
| JP | 2011-103361 | 5/2011 |
| JP | 2011093803 | 5/2011 |

\* cited by examiner

LIFT-OFF METHOD

BACKGROUND OF THE INVENTION

Field of the Invention

The present invention relates to a lift-off method for transferring an optical device layer in an optical device wafer to a transfer substrate, the optical device layer being formed on the front side of an epitaxy substrate such as a sapphire substrate and a silicon carbide substrate through a buffer layer.

Description of the Related Art

In an optical device fabrication process, an optical device layer composed of an n-type semiconductor layer and a p-type semiconductor layer is formed on the front side of a substantially disk-shaped epitaxy substrate such as a sapphire substrate and a silicon carbide substrate through a buffer layer. The optical device layer is formed of GaN (gallium nitride), InGaP (indium gallium phosphide), or AlGaN (aluminum gallium nitride). The optical device layer is partitioned by a plurality of crossing streets into a plurality of regions where a plurality of optical devices such as light emitting diodes and laser diodes are respectively formed, thus constituting an optical device wafer. The optical device wafer is divided along the streets to thereby obtain the individual optical devices.

Further, as a technique of improving the luminance of an optical device or improving the cooling thereof, Japanese Patent Laid-open No. 2004-72052 discloses a manufacturing method called lift-off for transferring the optical device layer of the optical device wafer to a transfer substrate formed of Mo, Cu, or Si, for example. The above-mentioned lift-off method includes the steps of bonding the transfer substrate through a bonding metal layer formed of Au—Sn (gold tin alloy), for example, to the optical device layer of the optical device wafer, next applying a laser beam having a wavelength (e.g., 257 nm) transmissive to the epitaxy substrate and absorptive to the buffer layer from the back side of the epitaxy substrate to the buffer layer, thereby breaking the buffer layer, and next peeling the epitaxy substrate from the optical device layer, thus transferring the optical device layer to the transfer substrate.

SUMMARY OF THE INVENTION

However, in bonding the transfer substrate through the bonding metal layer to the optical device layer of the optical device wafer to thereby form a composite substrate in the above lift-off method, the optical device wafer and the transfer substrate are heated to about 250° C. Accordingly, the composite substrate is slightly warped at room temperature because of a difference in coefficient of thermal expansion between the epitaxy substrate and the transfer substrate. Accordingly, in applying the laser beam to break the buffer layer, there is an area of the buffer layer where the laser beam is not applied because of spring back produced in the epitaxy substrate and the transfer substrate, so that the epitaxy substrate is peeled in such an unbroken area of the buffer layer, causing the damage to the optical device layer. As a result, there is a problem that the quality of the optical devices may be reduced.

It is therefore an object of the present invention to provide a lift-off method which can reliably peel off the epitaxy substrate without reducing the quality of the optical devices.

In accordance with an aspect of the present invention, there is provided a lift-off method for transferring an optical device layer in an optical device wafer to a transfer substrate, the optical device layer being formed on the front side of an epitaxy substrate through a buffer layer, the lift-off method including: a composite substrate forming step of bonding the transfer substrate through a bonding agent to the front side of the optical device layer of the optical device wafer, thereby forming a composite substrate; a buffer layer breaking step of applying a laser beam having a wavelength transmissive to the epitaxy substrate and absorptive to the buffer layer from the back side of the epitaxy substrate to the buffer layer after performing the composite substrate forming step, thereby breaking the buffer layer; and an optical device layer transferring step of peeling off the epitaxy substrate from the optical device layer after performing the buffer layer breaking step, thereby transferring the optical device layer to the transfer substrate; the buffer layer breaking step including a composite substrate heating step of heating the composite substrate to thereby relieve spring back produced in the epitaxy substrate and the transfer substrate prior to applying the laser beam to the buffer layer.

Preferably, the composite substrate is heated to 100 to 500° C. in the composite substrate heating step.

In the lift-off method according to the present invention, prior to applying the laser beam having a wavelength transmissive to the epitaxy substrate and absorptive to the buffer layer from the back side of the epitaxy substrate to the buffer layer in the buffer layer breaking step, the composite substrate heating step is performed to heat the composite substrate and thereby relieve the spring back produced in the epitaxy substrate and the transfer substrate constituting the composite substrate slightly warped at room temperature. Accordingly, since the spring back by the epitaxy substrate and the transfer substrate can be relieved, the buffer layer can be reliably broken. Further, in the optical device layer transferring step of peeling off the epitaxy substrate of the composite substrate to thereby transfer the optical device layer to the transfer substrate, there is no possibility that the epitaxy substrate may be peeled off in an unbroken area of the buffer layer. Accordingly, it is possible to solve the problem that the unbroken area of the buffer layer may cause the damage to the optical device layer in peeling the epitaxy substrate, causing a reduction in quality of the optical devices.

The above and other objects, features and advantages of the present invention and the manner of realizing them will become more apparent, and the invention itself will best be understood from a study of the following description and appended claims with reference to the attached drawings showing a preferred embodiment of the invention.

DETAILED DESCRIPTION OF THE PREFERRED EMBODIMENT

Figure 1A:
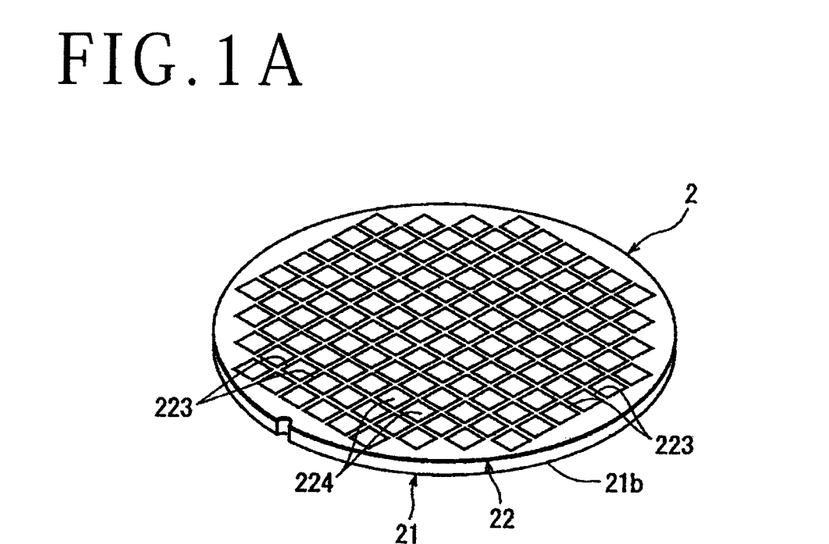
FIG. 1A is a perspective view of an optical device wafer having an optical device layer to be transferred to a transfer substrate by the lift-off method according to the present invention.

A preferred embodiment of the lift-off method according to the present invention will now be described in detail with reference to the attached drawings. FIG. 1A is a perspective view of an optical device wafer 2 having an optical device layer to be transferred to a transfer substrate by the lift-off method according to the present invention, and FIG. 1B is an enlarged sectional view of an essential part of the optical device wafer 2 shown in FIG. 1A.

Figure 1B:
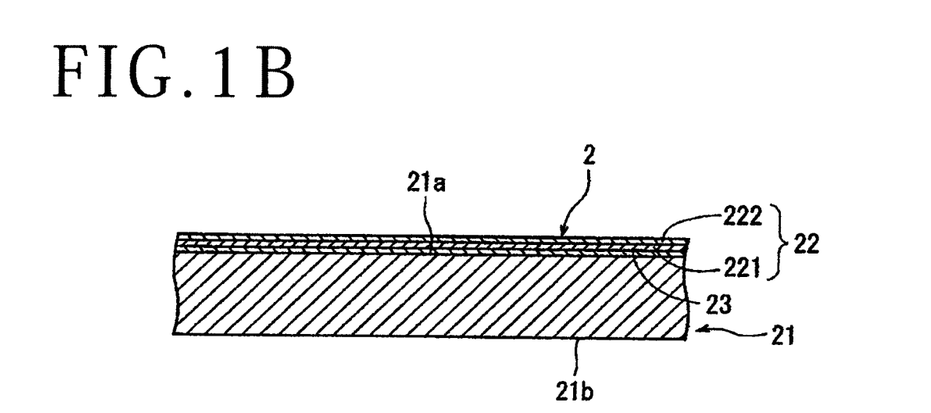
FIG. 1B is an enlarged sectional view of an essential part of the optical device wafer shown in FIG. 1A.

The optical device wafer 2 shown in FIGS. 1A and 1B is formed by epitaxial growth of an optical device layer 22 on the front side 21a of a circular epitaxy substrate 21. The epitaxy substrate 21 is formed from a sapphire substrate. The epitaxy substrate 21 has a diameter of 50 mm and a thickness of 600 μm, for example. The optical device layer 22 is composed of an n-type gallium nitride semiconductor layer 221 and a p-type gallium nitride semiconductor layer 222. In forming the optical device layer 22 composed of the n-type gallium nitride semiconductor layer 221 and the p-type gallium nitride semiconductor layer 222 on the front side 21a of the epitaxy substrate 21 by epitaxial growth, a buffer layer 23 of gallium nitride (GaN) is formed between the front side 21a of the epitaxy substrate 21 and the n-type gallium nitride semiconductor layer 221 forming the optical device layer 22. The buffer layer 23 has a thickness of 1 μm, for example, and the optical device layer 22 has a thickness of 10 μm, for example. As shown in FIG. 1A, the optical device layer 22 is partitioned by a plurality of crossing streets 223 to define a plurality of regions where a plurality of optical devices 224 are respectively formed.

Figure 2A:
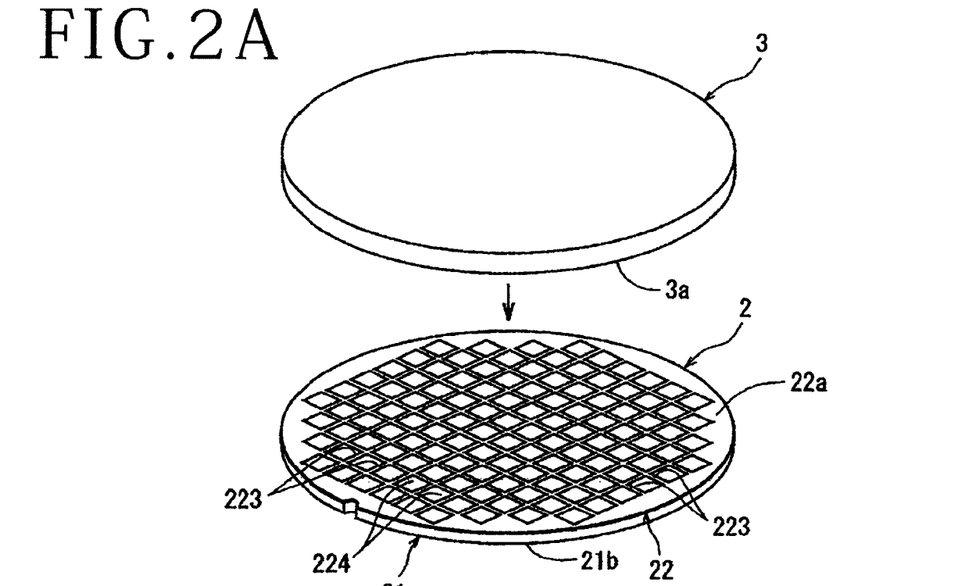
FIGS. 2A to 2C are views for illustrating a composite substrate forming step in the lift-off method according to the present invention.
Figure 2B:
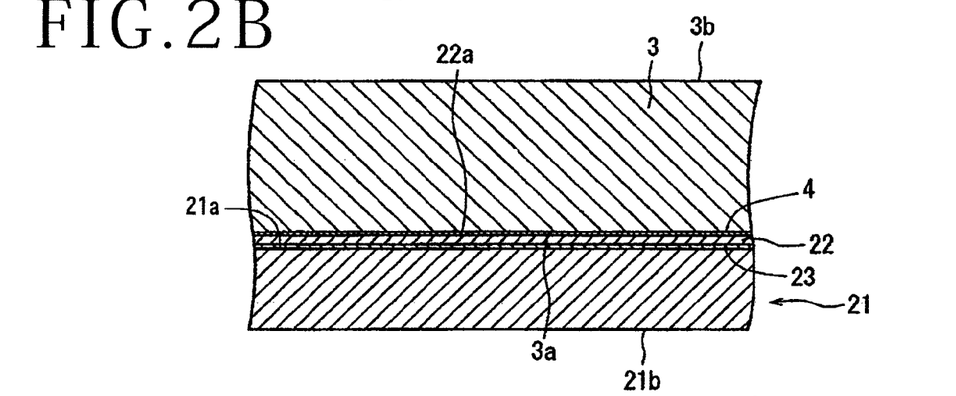
Figure 2C:
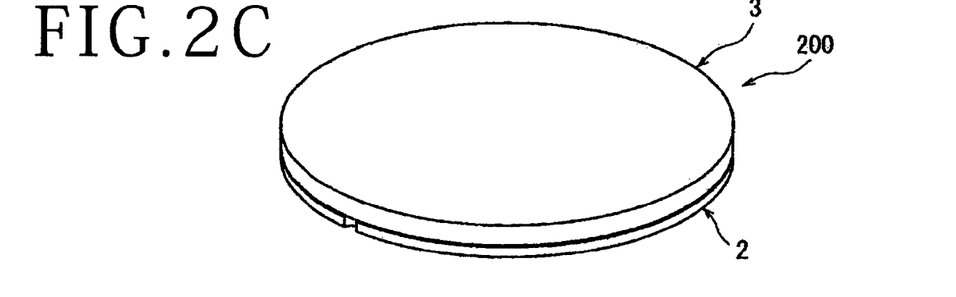

To peel off the epitaxy substrate 21 from the optical device layer 22 in the optical device wafer 2 and transfer the optical device layer 22 to a transfer substrate, a composite substrate forming step is first performed in such a manner that the transfer substrate is bonded to the front side 22a of the optical device layer 22 to thereby form a composite substrate. More specifically, as shown in FIGS. 2A to 2C, a transfer substrate 3 having a thickness of 1 mm, for example, is bonded through a bonding metal layer 4 as a bonding agent to the front side 22a of the optical device layer 22 formed on the front side 21a of the epitaxy substrate 21 constituting the optical device wafer 2. In this preferred embodiment, the transfer substrate 3 is formed of copper (Cu), and the bonding metal layer 4 is formed of gold tin alloy (Au—Sn). As other examples, the transfer substrate 3 may be formed of molybdenum (Mo) or silicon (Si), and the bonding metal layer 4 may be formed of gold (Au), platinum (Pt), chromium (Cr), indium (In), or palladium (Pd) as a bonding metal.

This composite substrate forming step is performed in the following manner. The bonding metal mentioned above is deposited by evaporation to the front side 22a of the optical device layer 22 formed on the front side 21a of the epitaxy substrate 21 or to the front side 3a of the transfer substrate 3, thereby forming the bonding metal layer 4 having a thickness of about 3 μm. Thereafter, the bonding metal layer 4 is brought into pressure contact with the front side 3a of the transfer substrate 3 or the front side 22a of the optical device layer 22, thereby bonding the front side 3a of the transfer substrate 3 through the bonding metal layer 4 to the front side 22a of the optical device layer 22 constituting the optical device wafer 2. As a result, a composite substrate 200 is formed as shown in FIG. 2C. In bonding the transfer substrate 3 to the front side 22a of the optical device layer 22 formed on the front side 21a of the epitaxy substrate 21 to thereby form the composite substrate 200 in the composite substrate forming step, the epitaxy substrate 21 and the transfer substrate 3 are heated to about 250° C. Accordingly, warpage slightly occurs in the composite substrate 200 at room temperature because of a difference in coefficient of thermal expansion between the epitaxy substrate 21 and the transfer substrate 3.

After performing the composite substrate forming step to bond the front side 3a of the transfer substrate 3 through the bonding metal layer 4 to the front side 22a of the optical device layer 22 of the optical device wafer 2 and thereby form the composite substrate 200 as mentioned above, a buffer layer breaking step is performed in such a manner that a laser beam having a wavelength transmissive to the epitaxy substrate 21 and absorptive to the buffer layer 23 is applied to the buffer layer 23 from the back side 21b of the epitaxy substrate 21 constituting the composite substrate 200, thereby breaking the buffer layer 23. This buffer layer breaking step is performed by using a laser processing apparatus 5 shown in FIG. 3. The laser processing apparatus 5 shown in FIG. 3 includes a stationary base 50, a chuck table mechanism 6 for holding a workpiece, the chuck table mechanism 6 being provided on the stationary base 50 so as to be movable in a feeding direction (X direction) shown by an arrow X, a laser beam applying unit supporting mechanism 7 provided on the stationary base 50 so as to be movable in an indexing direction (Y direction) shown by an arrow Y perpendicular to the X direction, and laser beam applying means 8 provided on the laser beam applying unit supporting mechanism 7 so as to be movable in a focal position adjusting direction (Z direction) shown by an arrow Z.

Figure 3:
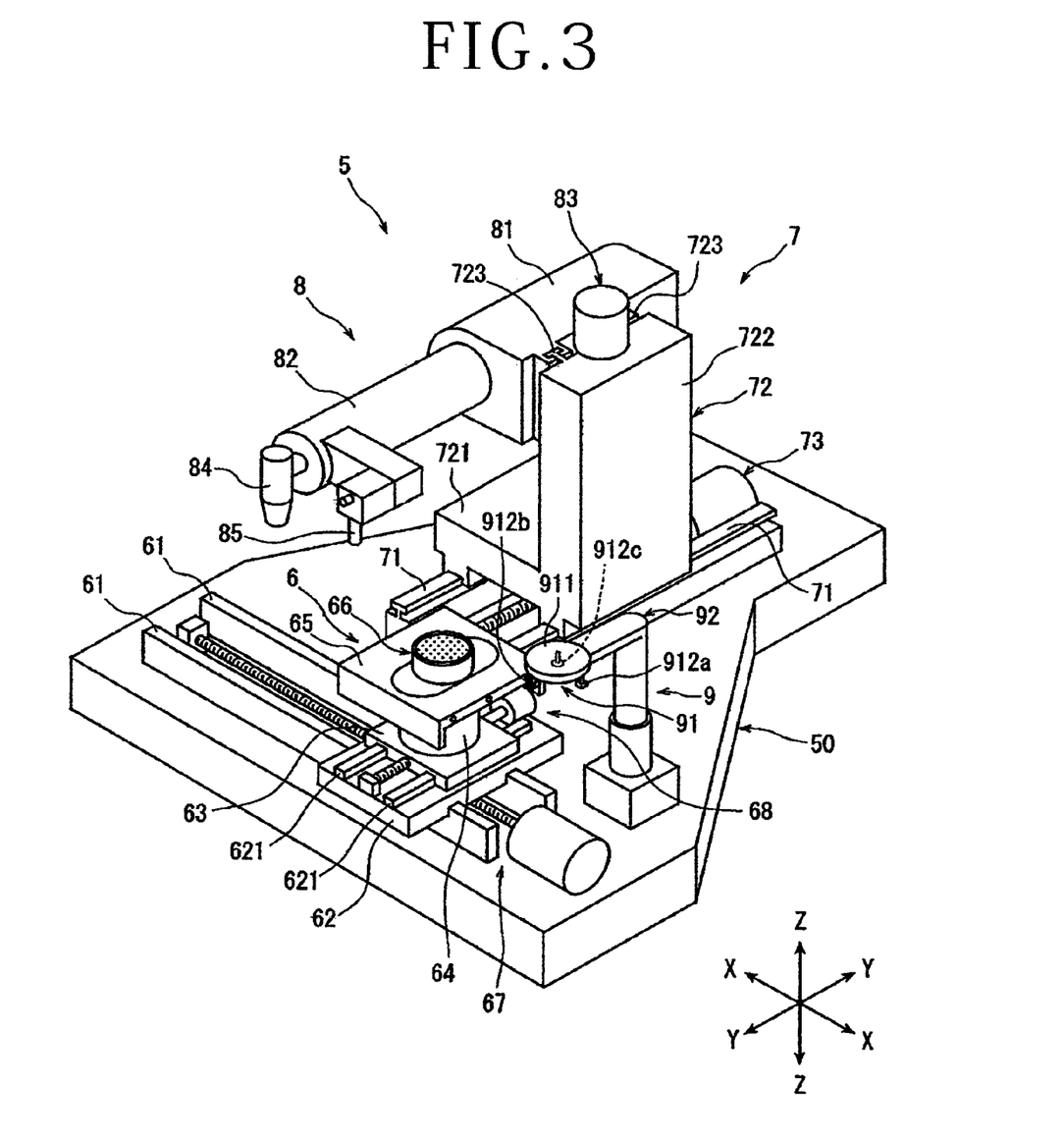
FIG. 3 is a perspective view of a laser processing apparatus for performing a buffer layer breaking step and an optical device layer transferring step in the lift-off method according to the present invention.
Figure 4:
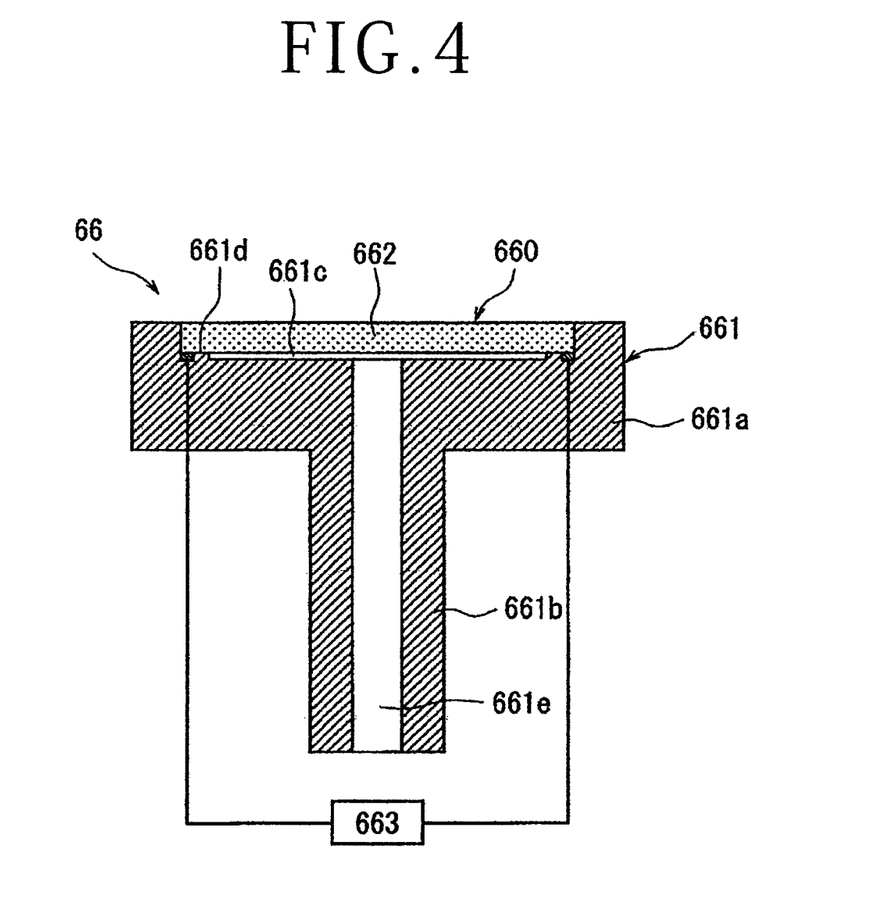
FIG. 4 is a sectional view of a chuck table included in the laser processing apparatus shown in FIG. 3.

The chuck table mechanism 6 includes a pair of guide rails 61 provided on the stationary base 50 so as to extend parallel to each other in the X direction, a first slide block 62 provided on the guide rails 61 so as to be movable in the X direction, a pair of guide rails 621 provided on the upper surface of the first slide block 62 so as to extend parallel to each other in the Y direction, a second slide block 63 provided on the guide rails 621 so as to be movable in the Y direction, a cylindrical member 64 standing on the upper surface of the second slide block 63, a cover table 65 supported by the cylindrical member 64, and a chuck table 66 as workpiece holding means. As shown in FIG. 4, the chuck table 66 is composed of a chuck table body 661 and a porous ceramic heater 662 provided in a holding area 660 of the chuck table body 661. The porous ceramic heater 662 functions as a suction holding member having porosity. The chuck table body 661 is composed of a disk-shaped holding portion 661a and a rotating shaft portion 661b projecting from the lower surface of the holding portion 661a. The chuck table body 661 is an integral member formed of metal such as stainless steel or ceramics, for example. A circular recess 661c for receiving the porous ceramic heater 662 is formed in the holding area 660 on the upper surface of the holding portion 661a. An annular support bed 661d for placing the porous ceramic heater 662 thereon is formed on the bottom of the circular recess 661c along the outer circumference thereof. A suction passage 611e opening to the circular recess 661c is formed in the holding portion 611a and the rotating shaft portion 611b of the chuck table body 661.

The porous ceramic heater 662 functioning as the suction holding member is fitted in the circular recess 661c formed on the upper surface of the holding portion 661a of the chuck table body 661 and placed on the annular support bed 661d formed on the bottom of the circular recess 661c. Further, the outer circumferential surface of the porous ceramic heater 662 is bonded to the inner circumferential surface of the circular recess 661c by any suitable adhesive. In the condition where the porous ceramic heater 662 is fitted in the circular recess 661c formed on the upper surface of the holding portion 661a of the chuck table body 661 as mentioned above, the upper surface of the porous ceramic heater 662 is flush with the upper surface of the holding portion 661a.

The suction passage 661e formed in the chuck table body 661 of the chuck table 66 is connected to suction means (not shown). Accordingly, when the workpiece is placed on the porous ceramic heater 662 provided in the holding area 660 of the chuck table body 661 and the suction means is next operated, a vacuum is applied through the suction passage 661e to the upper surface of the porous ceramic heater 662, thereby holding the workpiece on the upper surface of the porous ceramic heater 662 under suction.

The porous ceramic heater 662 constituting the chuck table 66 is connected to a power circuit 663. Accordingly, when electric power is applied from the power circuit 663 to the porous ceramic heater 662, the porous ceramic heater 662 is heated to a predetermined temperature. Preferably, the porous ceramic heater 662 is heated to 100 to 500° C.

Figure 5:
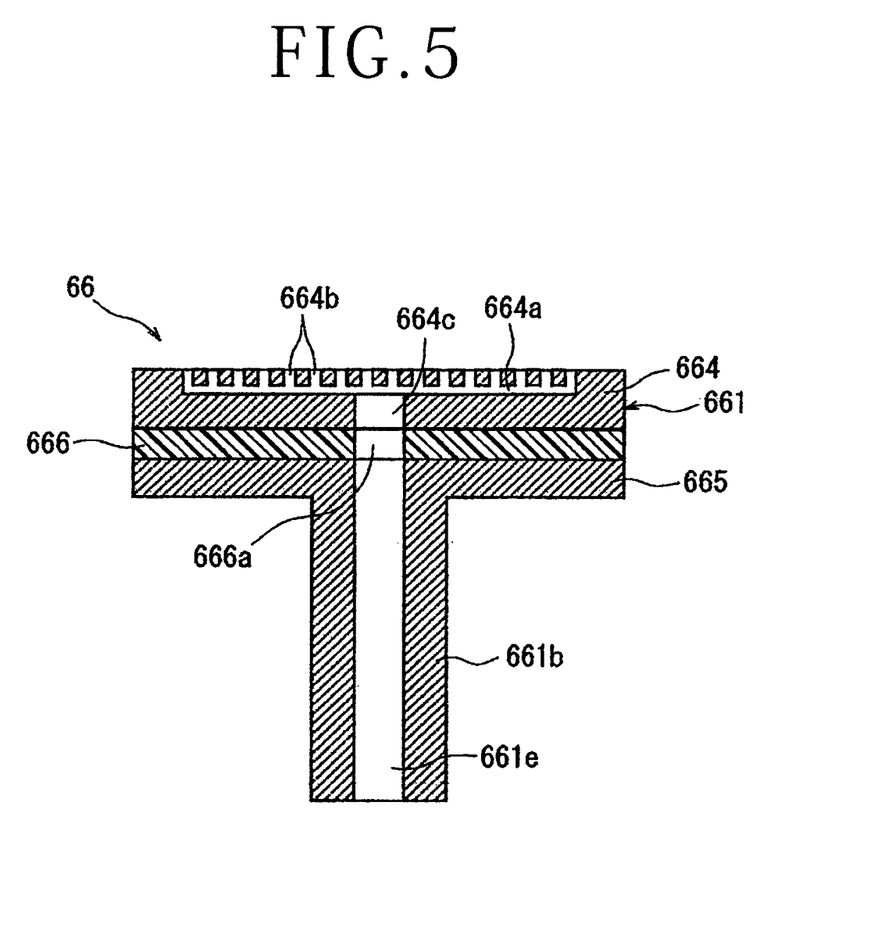
FIG. 5 is a sectional view showing a modification of the chuck table shown in FIG. 3.

A modification of the chuck table 66 will now be described with reference to FIG. 5. The chuck table body 661 of the chuck table 66 shown in FIG. 5 is composed of an upper member 664 and a lower member 665. A rubber heater 666 is interposed between the upper member 664 and the lower member 665. The upper member 664 is formed with a vacuum chamber 664a, a plurality of suction holes 664b communicating with the vacuum chamber 664a and opening to the upper surface of the upper member 664, and a communication hole 664c communicating with the vacuum chamber 664a and opening to the lower surface of the upper member 664. A rotating shaft portion 661b projects from the lower surface of the lower member 665. A suction passage 661e is formed in the lower member 665 and the rotating shaft portion 661b. The rubber heater 666 is formed with a communication passage 666a for making the communication between the communication hole 664c of the upper member 664 and the suction passage 661e of the lower member 665 and the rotating shaft portion 661b. The rubber heater 666 constituting the chuck table 66 is connected to a power circuit (not shown) like that shown in FIG. 4, so that the rubber heater 666 is heated to 100 to 500° C.

Referring back to FIG. 3, the chuck table 66 is rotatable by a pulse motor (not shown) provided in the cylindrical member 64. The chuck table mechanism 6 further includes feeding means 67 for moving the first slide block 62 in the X direction along the guide rails 61 and first indexing means 68 for moving the second slide block 63 in the Y direction along the guide rails 621. Each of the feeding means 67 and the first indexing means 68 is configured by a known ball screw mechanism.

The laser beam applying unit supporting mechanism 7 includes a pair of guide rails 71 provided on the stationary base 50 so as to extend parallel to each other in the Y direction and a movable support base 72 provided on the guide rails 71 so as to be movable in the Y direction. The movable support base 72 is composed of a horizontal portion 721 slidably supported to the guide rails 71 and a vertical portion 722 extending vertically upward from the upper surface of the horizontal portion 721. The movable support base 72 is movable in the Y direction along the guide rails 71 by second indexing means 73 configured by a known ball screw mechanism.

The laser beam applying means 8 includes a unit holder 81. The unit holder 81 is supported to the vertical portion 722 of the movable support base 72 so as to be movable in the Z direction along a pair of guide rails 723 provided on the vertical portion 722. The unit holder 81 supported to the vertical portion 722 is movable in the Z direction along the guide rails 723 by focal position adjusting means 83 configured by a known ball screw mechanism.

The laser beam applying means 8 further includes a cylindrical casing 82 fixed to the unit holder 81 so as to extend in a substantially horizontal direction. Although not shown, the casing 82 contains pulsed laser beam oscillating means including a pulsed laser beam oscillator and repetition frequency setting means. The laser beam applying means 8 further includes focusing means 84 mounted on the front end of the casing 82 for focusing a pulsed laser beam oscillated from the pulsed laser beam oscillating means. Imaging means 85 is provided at the front end portion of the casing 82 to image the workpiece held on the chuck table 66 and to be laser-processed by the laser beam applying means 8. The imaging means 85 is configured by optical means including a microscope and a CCD camera. An image signal output from the imaging means 85 is transmitted to control means (not shown).

The laser processing apparatus 5 further includes a peeling mechanism 9 for peeling the epitaxy substrate 21 of the optical device wafer 2 from the optical device layer 22. The peeling mechanism 9 is composed of suction holding means 91 for holding the epitaxy substrate 21 under suction in the condition where the optical device wafer 2 held on the chuck table 66 is set in a peeling position and supporting means 92 for vertically movably supporting the suction holding means 91. The peeling mechanism 9 is located on one side of the chuck table mechanism 6. The suction holding means 91 is composed of a holding member 911 and a plurality of (three in this preferred embodiment) suction pads 912a, 912b, and 912c mounted on the lower side of the holding member 911. The suction pads 912a to 912c are connected to suction means (not shown).

In performing the buffer layer breaking step by using the laser processing apparatus 5 mentioned above to apply a laser beam having a wavelength transmissive to the epitaxy substrate 21 and absorptive to the buffer layer 23 from the back side 21b of the epitaxy substrate 21 of the composite substrate 200 to the buffer layer 23, thereby breaking the buffer layer 23, the transfer substrate 3 of the composite substrate 200 is placed on the upper surface of the porous ceramic heater 662 of the chuck table 66 shown in FIG. 4 or on the upper surface of the upper member 664 of the chuck table body 661 of the chuck table 66 shown in FIG. 5. Thereafter, electric power is applied to the porous ceramic heater 662 or the rubber heater 666 constituting the chuck table 66 to thereby heat the porous ceramic heater 662 or the rubber heater 666 to 100 to 500° C. As a result, the composite substrate 200 placed on the chuck table 66 is heated to 100 to 500° C. (composite substrate heating step). Accordingly, it is possible to relieve spring back produced in the epitaxy substrate 21 and the transfer substrate 3 constituting the composite substrate 200 slightly warped at room temperature.

Figure 6A:
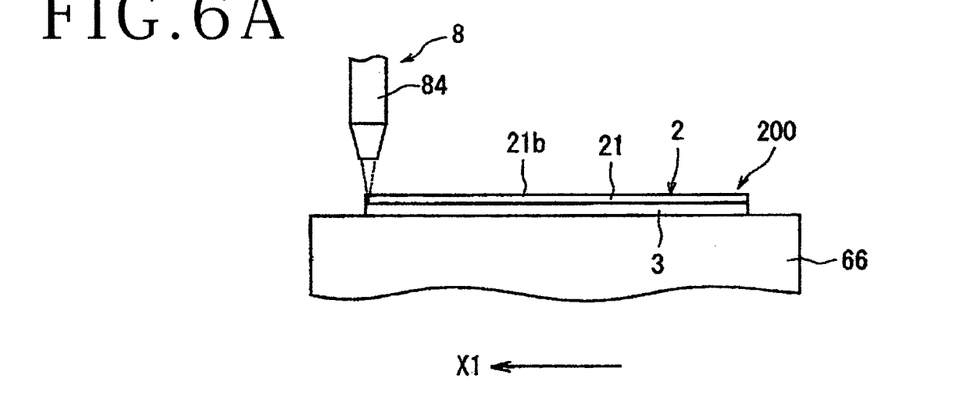
FIGS. 6A to 6C are views for illustrating the buffer layer breaking step.
Figure 6B:
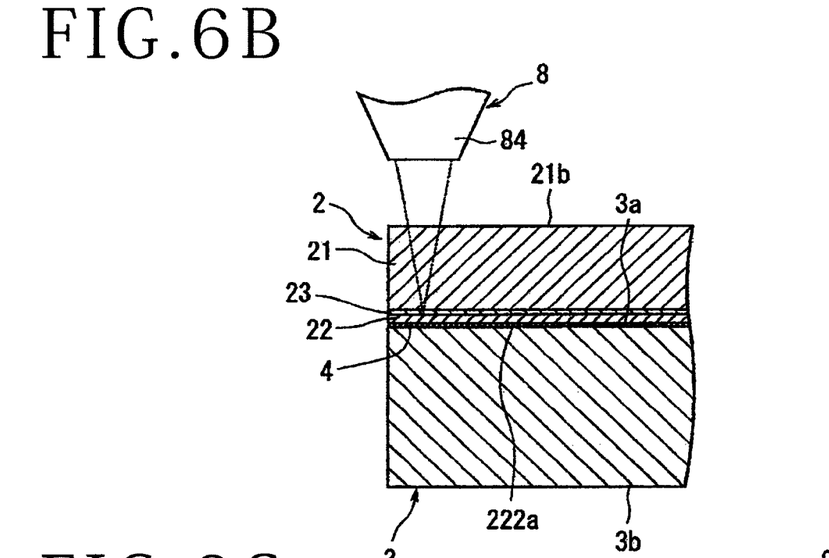

After performing the composite substrate heating step mentioned above, the suction means (not shown) connected to the chuck table 66 is operated to hold the composite substrate 200 on the chuck table 66 under suction (wafer holding step). Accordingly, the composite substrate 200 is held on the chuck table 66 under suction in the condition where the back side 21b of the epitaxy substrate 21 of the optical device wafer 2 is oriented upward. After performing the wafer holding step mentioned above, the feeding means 67 is operated to move the chuck table 66 to a laser beam applying area below the focusing means 84 of the laser beam applying means 8 so that one end (left end as viewed in FIG. 6A) of the epitaxy substrate 21 of the optical device wafer 2 constituting the composite substrate 200 held on the chuck table 66 is positioned directly below the focusing means 84 of the laser beam applying means 8 as shown in FIG. 6A.

Figure 6C:
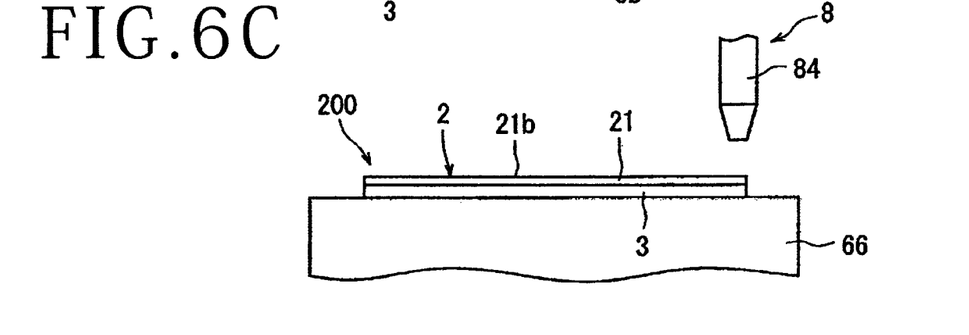

Thereafter, the laser beam applying means 8 is operated to apply the pulsed laser beam from the focusing means 84 to the buffer layer 23, wherein the pulsed laser beam has a wavelength transmissive to the epitaxy substrate 21 (sapphire) and absorptive to the buffer layer 23 (GaN). At the same time, the chuck table 66 is moved in the direction shown by an arrow X1 in FIG. 6A at a predetermined feed speed. When the other end (right end as viewed in FIG. 6C) of the epitaxy substrate 21 reaches the position directly below the focusing means 84 of the laser beam applying means 8 as shown in FIG. 6C, the application of the pulsed laser beam is stopped and the movement of the chuck table 66 is also stopped. This buffer layer breaking step is repeatedly performed over the entire surface of the buffer layer 23.

As a modification, the buffer layer breaking step may be performed in the following manner. First, the focusing means 84 is positioned directly above the outer circumference of the epitaxy substrate 21 as shown in FIG. 6A. Thereafter, the pulsed laser beam is applied from the focusing means 84 and the focusing means 84 is moved toward the center of the chuck table 66 as rotating the chuck table 66, thereby applying the pulsed laser beam over the entire surface of the buffer layer 23.

For example, the buffer layer breaking step mentioned above is performed under the following processing conditions.

Light source: YAG laser
Wavelength: 257 nm
Repetition frequency: 50 kHz
Average power: 0.12 W
Pulse width: 100 ns
Spot diameter: 70 μm
Defocus: 1.0 mm (in the condition where the focal point of the laser beam is set on the back side 21b of the epitaxy substrate 21, the focusing means 84 is moved toward the epitaxy substrate 21 by 1 mm.)
Work feed speed: 600 mm/second By performing the buffer layer breaking step under the above processing conditions, the buffer layer 23 is broken. Prior to operating the laser beam applying means 8 to apply the pulsed laser beam having a wavelength transmissive to the epitaxy substrate 21 (sapphire) and absorptive to the buffer layer 23 (GaN) from the focusing means 84 to the buffer layer 23 in the above buffer layer breaking step, the composite substrate heating step is performed to heat the composite substrate 200 held on the chuck table 66 under suction and thereby relieve the spring back produced in the epitaxy substrate 21 and the transfer substrate 3 constituting the composite substrate 200 slightly warped at room temperature. Accordingly, since the spring back by the epitaxy substrate 21 and the transfer substrate 3 can be relieved, the buffer layer 23 can be reliably broken.

Figure 7A:
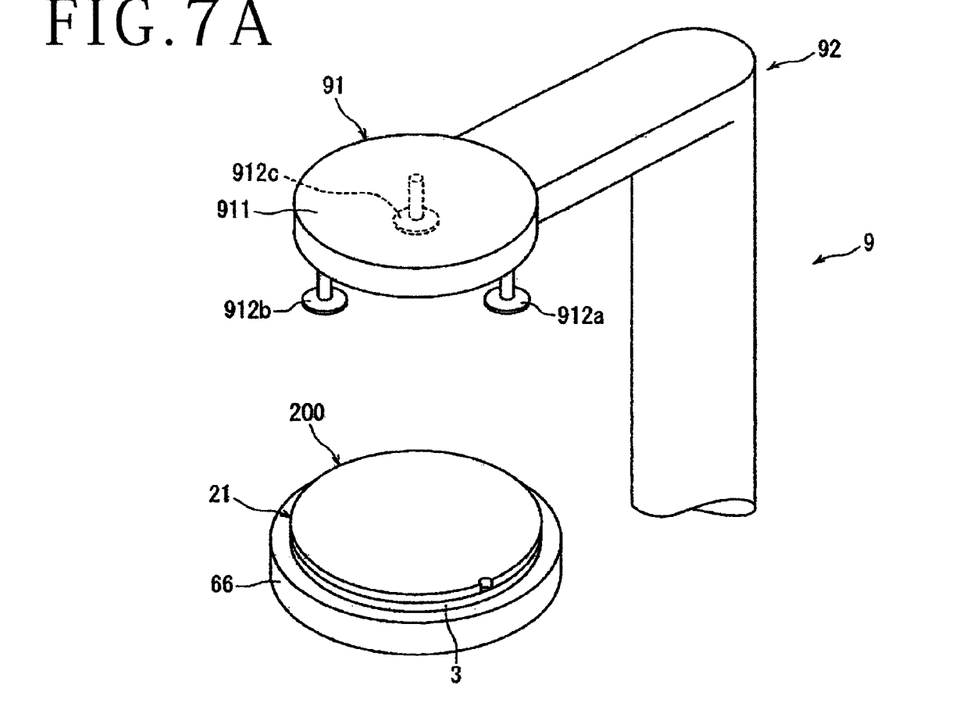
FIGS. 7A and 7B are perspective views for illustrating an epitaxy substrate sucking step in the optical device layer transferring step.
Figure 7B:
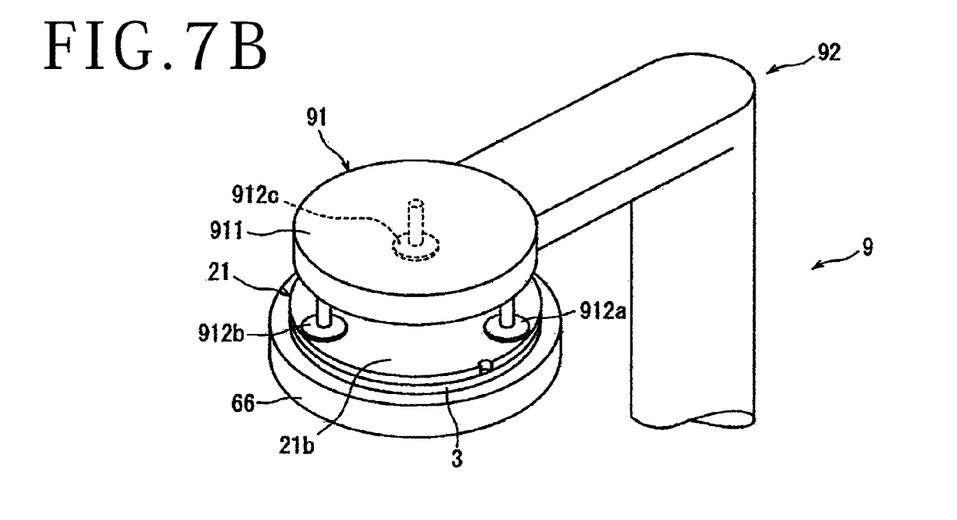

After performing the buffer layer breaking step mentioned above, an optical device layer transferring step is performed in such a manner that the epitaxy substrate 21 of the composite substrate 200 is peeled off to thereby transfer the optical device layer 22 to the transfer substrate 3. More specifically, the chuck table 66 holding the composite substrate 200 is moved to the peeling position where the peeling mechanism 9 is located, so that the composite substrate 200 held on the chuck table 66 is positioned directly below the suction holding means 91 of the peeling mechanism 9 as shown in FIG. 7A. Thereafter, as shown in FIG. 7B, the suction holding means 91 is lowered to bring the suction pads 912a to 912c into contact with the back side 21b of the epitaxy substrate 21, and the suction means (not shown) connected to the suction pads 912a to 912c is operated to hold the back side 21b of the epitaxy substrate 21 under suction through the suction pads 912a to 912c (epitaxy substrate sucking step).

Figure 8:
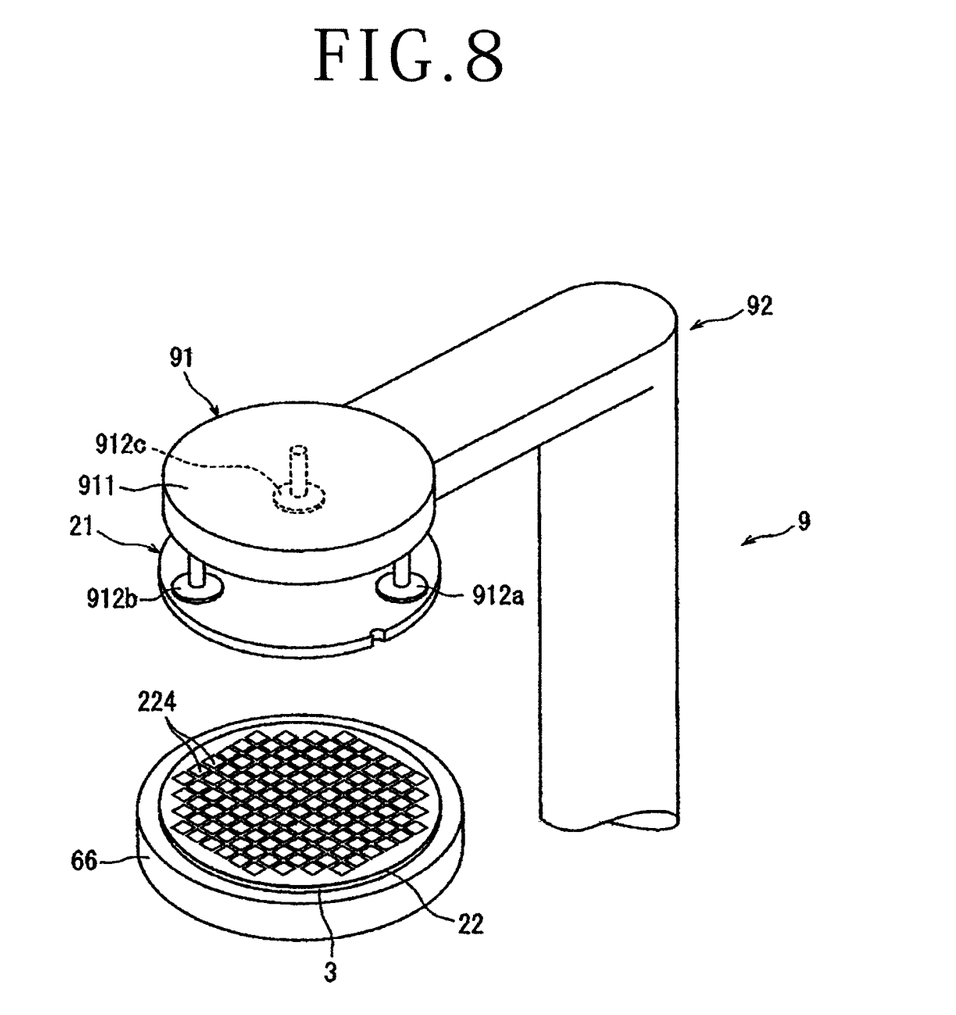
FIG. 8 is a perspective view for illustrating a peeling step in the optical device layer transferring step.

After performing the epitaxy substrate sucking step mentioned above, the suction pads 912a to 912c sucking the epitaxy substrate 21 is moved away from the transfer substrate 3 to thereby peel off the epitaxy substrate 21, thereby transferring the optical device layer 22 to the transfer substrate 3 (peeling step). More specifically, after performing the epitaxy substrate sucking step as shown in FIG. 7B, the suction holding means 91 is raised as shown in FIG. 8 to thereby peel the epitaxy substrate 21 from the optical device layer 22. As a result, the optical device layer 22 is transferred from the epitaxy substrate 21 to the transfer substrate 3. In this manner, the composite substrate 200 is subjected to the optical device layer transferring step composed of the epitaxy substrate sucking step and the peeling step. Since the buffer layer 23 in the composite substrate 200 is reliably broken in the buffer layer breaking step, there is no possibility that the epitaxy substrate 21 may be peeled off in an unbroken area of the buffer layer 23. Accordingly, it is possible to solve the problem that the unbroken area of the buffer layer 23 may cause the damage to the optical device layer 22 in peeling the epitaxy substrate 21, causing a reduction in quality of the optical devices.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. A lift-off method for transferring an optical device layer in an optical device wafer to a transfer substrate, said optical device layer being formed on a front side of an epitaxy substrate through a buffer layer, said lift-off method comprising:

a composite substrate forming step of bonding said transfer substrate through a bonding agent to the front side of said optical device layer of said optical device wafer, thereby forming a composite substrate;

a buffer layer breaking step of applying a laser beam having a wavelength transmissive to said epitaxy substrate and absorptive to said buffer layer from a back side of said epitaxy substrate to said buffer layer after performing said composite substrate forming step, thereby breaking said buffer layer; and an optical device layer transferring step of peeling off said epitaxy substrate from said optical device layer after performing said buffer layer breaking step, thereby transferring said optical device layer to said transfer substrate;

said buffer layer breaking step including a composite substrate heating step of heating said composite substrate to thereby relieve spring back produced in said epitaxy substrate and said transfer substrate prior to applying said laser beam to said buffer layer.

2. The lift-off method according to claim 1, wherein said composite substrate is heated to a temperature between 100° C. and 500° C. in said composite substrate heating step.

3. The lift-off method according to claim 1, wherein:
said buffer layer breaking step is performed with said composite substrate positioned upon a chuck table such that a back side of the transfer substrate faces the chuck table; and
said composite substrate heating step includes using a heater positioned within said chuck table.

4. The lift-off method according to claim 3, wherein said heater comprises a porous ceramic heater.

5. The lift-off method according to claim 3, wherein said heater comprises a rubber heater.

6. A lift-off method for transferring an optical device layer in an optical device wafer to a transfer substrate, said optical device layer being formed on a front side of an epitaxy substrate through a buffer layer, said lift-off method comprising:
a composite substrate forming step of bonding said transfer substrate through a bonding agent to the front side of said optical device layer of said optical device wafer, thereby forming a composite substrate;
a buffer layer breaking step of applying a laser beam from a laser beam applying means through a focusing means, wherein the laser beam has a wavelength transmissive to said epitaxy substrate and absorptive to said buffer layer, to said buffer layer from a back side of said epitaxy substrate after performing said composite substrate forming step, thereby breaking said buffer layer; and
an optical device layer transferring step of peeling off said epitaxy substrate from said optical device layer after performing said buffer layer breaking step, thereby transferring said optical device layer to said transfer substrate;
said buffer layer breaking step including a composite substrate heating step of using a heater to heat said composite substrate, from a back side of the transfer substrate, to thereby relieve spring back produced in said epitaxy substrate and said transfer substrate,
wherein said focusing means and said heater are located on opposite sides of said composite substrate during said buffer layer breaking step.

7. The lift-off method according to claim 6, wherein said composite substrate is heated to a temperature between 100° C. and 500° C. in said composite substrate heating step.

8. The lift-off method according to claim 6, wherein said heating step is performed prior to applying said laser beam to said buffer layer.

9. The lift-off method according to claim 6, wherein:
said buffer layer breaking step is performed with said composite substrate positioned upon a chuck table such that the back side of the transfer substrate faces the chuck table; and
said composite substrate heating step includes using a heater positioned within said chuck table.

10. The lift-off method according to claim 9, wherein said heater comprises a porous ceramic heater.

11. The lift-off method according to claim 9, wherein said heater comprises a rubber heater.

\* \* \* \* \*